US00PP24069P3

(12) United States Plant Patent
Dobres

(10) Patent No.: US PP24,069 P3
(45) Date of Patent: Dec. 10, 2013

(54) SHRUB ROSE PLANT NAMED 'RADNOV'

(50) Latin Name: *Rosa hybrida*
Varietal Denomination: Radnov

(75) Inventor: Michael S. Dobres, Philadelphia, PA (US)

(73) Assignee: Novaflora Inc., West Grove, PA (US)

( * ) Notice: Subject to any disclaimer, the term of this patent is extended or adjusted under 35 U.S.C. 154(b) by 413 days.

(21) Appl. No.: 12/923,582

(22) Filed: Sep. 29, 2010

(65) Prior Publication Data

US 2012/0079637 P1 Mar. 29, 2012

(51) Int. Cl.
*A01H 5/00* (2006.01)

(52) U.S. Cl.
USPC ..... Plt./107

(58) Field of Classification Search
USPC ..... Plt./107, 137, 148
See application file for complete search history.

(56) References Cited

U.S. PATENT DOCUMENTS

PP18,507 P3 * 2/2008 Cockcroft et al. ..... Plt./107

OTHER PUBLICATIONS

Walther et al. In vitro mutagenesis in roses. Acta Horticulturae 189, 1986, 37-46.*

* cited by examiner

*Primary Examiner* — June Hwu
(74) *Attorney, Agent, or Firm* — Buchanan Ingersoll & Rooney PC

(57) ABSTRACT

A new and distinct shrub rose plant is provided that abundantly and substantially continuously forms attractive double blossoms that are light pink in coloration. The plant exhibits vigorous upright and bushy growth habit. The foliage is medium green with a satiny finish. Good disease resistance combined with good winter hardiness is displayed. The plant is well suited for growing as attractive ornamentation in parks and gardens.

1 Drawing Sheet

Botanical/commercial classification: *Rosa hybrida*/Shrub Rose Plant.

Varietal denomination: Cv. Radnov.

SUMMARY OF THE INVENTION

The new variety of *Rosa hybrida* rose plant was derived from the 'Radtkopink' variety (U.S. Plant Pat. No. 18,507) through the use of induced mutagenesis followed by selection. More specifically, during September 2005 tissue cultured shoots of the 'Radtkopink' variety were subjected to gamma irradiation to form a population of plants which included various mutants. These plants were thereafter grown in a greenhouse at West Grove, Pa., U.S.A., and were carefully evaluated. A single plant of the present invention was selected during June 2006 from among the resulting plants primarily in view of its distinctive light pink blossom coloration combined with other attractive traits.

It was found that the new shrub rose plant of the present invention possesses the following combination of characteristics:

(a) abundantly and substantially continuously forms attractive double blossoms that are light pink in coloration,
(b) exhibits an upright and bushy growth habit,
(c) forms vigorous vegetation,
(d) forms attractive medium green foliage with a satiny finish,
(e) exhibits good disease resistance, and
(f) is well suited for providing attractive ornamentation in the landscape.

The winter hardiness of the new variety has been found to be very good during observations to date. The blooming cycle of the new variety has proven to be generally comparable to that of the 'Radtkopink' variety.

The new variety well meets the needs of the horticultural industry. It can be grown to advantage as attractive ornamentation in parks, gardens, public areas, and in residential settings. The new variety is particularly well suited for providing attractive ornamentation in the landscape. The light pink blossoms contrast nicely with the satiny medium green foliage.

The new variety of the present invention can be readily distinguished from plants of the 'Radtko' variety (U.S. Plant Pat. No. 16,202), and the 'Radtkopink' variety (U.S. Plant Pat. No. 18,507) upon an inspection of the blossoms. More specifically, the 'Radtko' variety forms bright red blossoms, and the 'Radtkopink' variety forms bright pink blossoms that are substantially darker in coloration than the light pink blossoms of the new variety of the present invention.

The characteristics of the new variety have been found at Waso, Calif., U.S.A. and at West Grove, Pa., U.S.A., to be homogeneous and stable and to be strictly transmissible by asexual propagation, including the rooting of cuttings from one generation to another. The new variety reproduces in a true-to-type manner by such asexual propagation.

The new variety has been named 'Radnov' and will be marketed in the United States under the BUBBLE DOUBLE trademark.

BRIEF DESCRIPTION OF THE PHOTOGRAPH

The accompanying photograph shows, as nearly true as it is reasonably possible to make the same in a color illustration of this character, typical specimens of the new variety.

The illustrated rose plants of the new variety were approximately three years of age and were observed during June while growing outdoors on their own roots at West Grove, Pa., U.S.A.

DETAILED DESCRIPTION

The chart used in the identification of colors is that of The Royal Horticultural Society (R.H.S. Colour Chart—1995 Edition or equivalent), London, England. The description is based on the observation of two-year-old specimens of the new variety during August while growing outdoors in containers on their own roots at West Grove, Pa., U.S.A.

Class: Landscape Shrub.

Plant:

*Height.*—Approximately 1 meter on average at the end of the growing season.

*Width.*—Approximately 1 meter on average at the end of one growing season.

*Habit.*—Upright and bushy.

Branches:

*Color.*—Young stems: near Yellow-Green Group 144A. Adult wood: Yellow-Green Group 146A.

*Texture.*—Generally smooth when young and when mature.

*Thorns.*—Size: approximately 7 to 9 mm in length on average, commonly with some smaller prickles near the peduncle, commonly approximately 4 per branch on average, oblong at the base and tapering to a fine point at the apex, near Yellow-green Group 145A in coloration when immature, and near Greyed-Orange Group 177B in coloration when mature.

Leaves:

*Size.*—A three-leaflet leaf commonly is approximately 7 to 10 cm in length on average including the petiole and approximately 5 cm in width on average, and a five-leaflet leaf commonly is approximately 5 cm in length on average including the petiole and approximately 7 to 8 cm in width on average.

*Leaflets.*—Number 3, 5 and 7. Length: approximately 2 to 4 cm on average. Width: approximately 2 cm on average at the widest point. Shape: ovate with a rounded base. Margins: serrulate. Texture: smooth on both surfaces, leathery, and with a coarse midrib on the under surface. Overall appearance: very dense, leathery, and medium green with a satiny finish. Color (young foliage): upper surface: commonly Green Group 137A, and with some reddish coloration of Greyed-Red Group 178B. under surface: commonly Yellow-Green Group 146B, and with some reddish coloration of Greyed-Red Group 178B. Color (adult foliage): upper surface: commonly Yellow-Green Group 147A. under surface: commonly Yellow-Green Group 147B.

*Stipules.*—Length: approximately 12 mm on average. Width: approximately 5 mm on average with the auricle facing outwards. Texture: smooth on both surfaces. Color: near Yellow-Green Group 144B.

*Petioles.*—Upper surface: near Yellow-Green Group 144A in coloration with some prickles. under surface: near Green Group 139D. length: commonly approximately 18 mm on average.

*Rachis.*—Upper surface: near Yellow-Green Group 144A. Under surface: near Yellow-Green Group 144A. Length: commonly approximately 4 to 6 mm on average.

Inflorescence:

*Number of flowers.*—In clusters sometimes with up to approximately 24 to 26 blooms per cluster.

*Peduncle.*—Superior strength with the blossoms often being held upright, medium green, near Yellow-Green Group 141D in coloration, commonly approximately 6 cm in length on average, approximately 3 mm in diameter on average, and commonly bears some prickles.

*Pedicels.*—Length: commonly approximately 3.5 cm on average. Diameter: commonly approximately 2 mm on average. Texture: smooth. Color: near Yellow-Green Group 146C.

*Sepals.*—Upper surface: commonly near Yellow-Green Group 144A in coloration. under surface: commonly near Yellow-Green Group 138C in coloration. Size: commonly approximately 2.5 cm in length on average, and approximately 9 mm in width on average at the base. Number: five. Extensions: commonly approximately 2 sepals bear approximately 2 to 6 extensions of varied lengths of approximately 5 to 9 mm. Texture: commonly bears some fine hairs at the edges. Apex: generally acuminate.

*Buds.*—Shape: slender. Size: small to medium. Length: approximately 2.5 cm on average as the calyx breaks. Color: commonly near Red-Purple Group 58C at the apex blending to Yellow-White Group 158C towards the base.

*Flower.*—Form: double and somewhat informal. Diameter: commonly approximately 7 cm on average when open. Depth: commonly approximately 2.5 cm on average when open. Color (when opening begins): upper surface: Red-Purple Group 62D. under surface: Red-Purple Group 65D. Color (when blooming): upper surface: Red Group 49A. under surface: Red Group 37C. Color (at end of blooming): upper surface: Red Group 36D commonly blending to Yellow-White Group 158C at the base. under surface: near Red Group 49C commonly blending to Yellow-White Group 158C at the base. Fragrance: very light sweet scent. Petal number: commonly approximately 40 to 45 on average. Petaloids: none observed. Petal shape: commonly wedge-shaped with a curled apex. Petal apex: cuspidate. Petal base: cuneate. Petal size: commonly approximately 3 cm in length on average and approximately 2 cm in width on average. Petal drop: the petals commonly drop cleanly and freely at full maturity; however, during hot humid weather there is some tendency for the petals to remain attached. Lastingness: the blossoms commonly last approximately two weeks on the plant depending upon environmental conditions, and up to approximately 5 days or more when cut and placed in a vase. Stamen: approximately 113 on average, and regularly arranged about the pistils. Anthers: approximately 3 mm in length on average, approximately 1.8 mm in width on average, and Yellow-Orange Group 22A in coloration. Filaments: approximately 6.3 mm in length, and near Red Group 48D in coloration. Pistils: separate and free, and approximately 36 on average. Styles: commonly approximately 5.5 mm in length, and near Red Group 45B in coloration. Stigmas: approximately 0.8 mm in diameter, and near Yellow Group 13C in coloration. Receptacle: generally rounded, smooth, approximately 13 mm in length on average, approximately 9 mm in width on average, near Yellow-Green Group 144B in coloration, and with achenes standing on the bottom and wall.

Development:

*Vegetation.*—Vigorous and strong.

*Blossoming.*—Early, abundant and substantially continuous during the growing season.

*Resistance to disease.*—Very good, with resistance to Blackspot, Mildew, and Rust having been displayed during observations to date.

*Hardiness.*—Very good, with plants having over-wintered at West Grove, Pa., U.S.A. in U.S.D.A. Hardiness Zone No. 6b.

*Formation of hips/seeds.*—Sparse.

I claim:

1. A new and distinct shrub rose plant characterized by the following combination of characteristics:

(a) abundantly and substantially continuously forms attractive double blossoms that are light pink in coloration,
(b) exhibits an upright and bushy growth habit,
(c) forms vigorous vegetation,
(d) forms attractive medium green foliage with a satiny finish,
(e) exhibits good disease resistance, and
(f) is well suited for providing attractive ornamentation in the landscape;

substantially as herein shown and described.

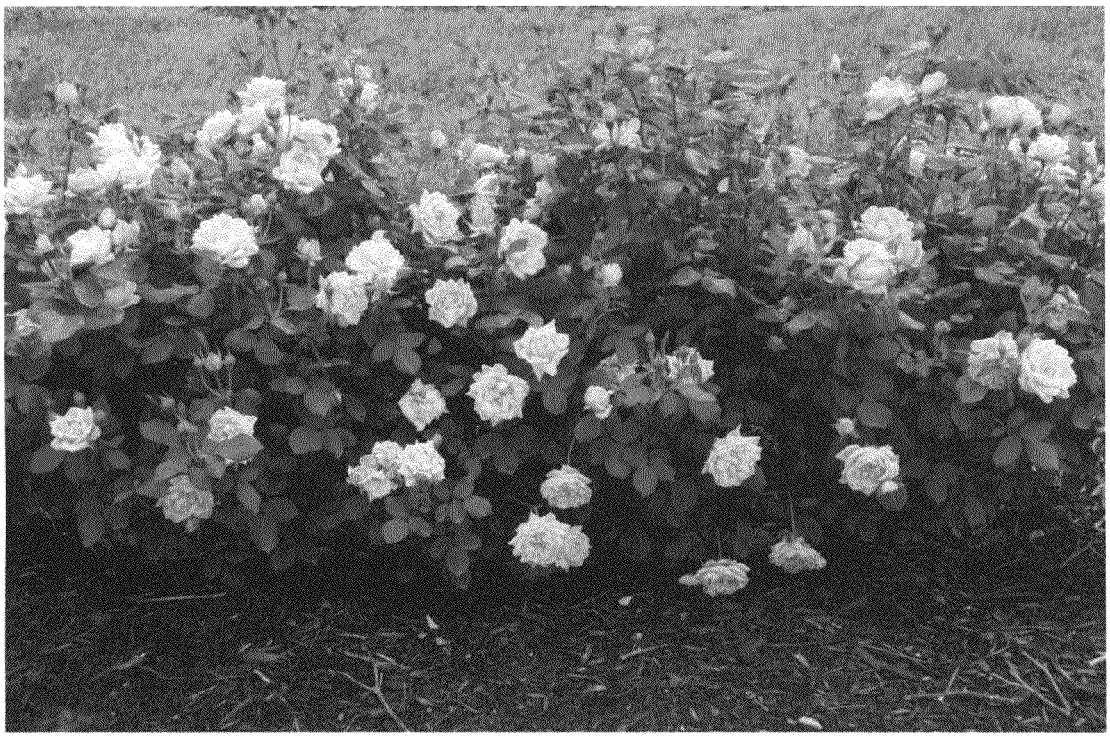

* * * * *